United States Patent [19]
Bowman

[11] Patent Number: 6,166,306
[45] Date of Patent: Dec. 26, 2000

[54] METHOD OF PRODUCING HYBRID CATHARANTHUS USING MALE STERILITY

[75] Inventor: Robert N. Bowman, Gilroy, Calif.

[73] Assignee: Goldsmith Seeds, Inc., Gilroy, Calif.

[21] Appl. No.: 09/176,949

[22] Filed: Oct. 22, 1998

[51] Int. Cl.[7] .............................. A01H 5/00; A01H 5/10; A01H 1/04
[52] U.S. Cl. ..................... 800/323; 800/260; 800/271; 800/274; 800/298; 800/303; Plt./226; 435/410
[58] Field of Search ..................................... 800/274, 271, 800/298, 303, 323, 260; Plt./263, 226; 435/410

[56] References Cited

U.S. PATENT DOCUMENTS 5,491,285  2/1996  Bowman ................................. 800/200

OTHER PUBLICATIONS

Dawson et al. Canadian Journal of Botany. vol. 71, pp. 629–638, 1993.
Gottschalk et al. Induced Mutations in Plant Breeding. Springer–Verlag, Berlin. Chapter 7, pp. 65–70, 1983.
Kaul. Male Sterility in Higher Plants. Springer–Verlag, Berlin. Chapter 2, pp. 15–32, 1988.
Reynaerts et al. Scientia Horticulturae. vol. 55:125–139, 1993.
Umbeck et al. Crop Science. vol. 23:584–588, 1983.
deHalac, Ines Noher, et al., "Pollen ontogenesis in *Oenothera*: a comparison of genotypically normal anthers with the male–sterile mutant *sterilis*," 3:41–53 Sex Plant Reprod (1990).
Kik, C., et al., "Analysis of genic male sterility in *Brassica oleracea*," 68:53–57 (1993).
Oard, James H., et al., "Inheritance and characterization of pollen fertility in phtoperiodically sensitive rice mutants," *Euphytica* 82:17–23 (1995).
Shifriss, Chen, et al., "Digenic nature of male sterility in pepper (*Capsicum annuum L.*)," *Euphytica* 67:111–112 (1993).
Singh, Indra Sen, "Induced Pollen Sterility in Petunia. Mode of Inheritance and Tapetal Behavior,"*Ann. Amélior. Plantes*, 25:303–315 (1975).
Tsuchiya, Tohru, et al., "Tapetum–Specific Expression of the Gene for an Endo–$\beta$–1,3–glucanase Causes Male Sterility in Transgenic Tobacco," *Plant Cell Physiol.* 36(3):487–494 (1995).
van der Meer, Ingrid M. et al., "Antisense Inhitibion of Favonoid Biosynthesis in Petunia Anthers Results in Male Sterility," *The Plant Cell*, 4:253–262, Mar., 1992.
Vedel, Fernand, et al., "Molecular basis of nuclear and cytoplasmic male sterility in higher plants," *Plant Physiol. Biochem.*, 32(5):601–618 (1994).
Xu, Huiling, et al., "Bcp1, a gene required for male fertility in Arabidopsis," Proc. Natl. Acad. Sci. USA, 92:2106–2110, Mar., 1995.
Zhuping, Yang, "Inheritance of photoperiod sensitive genic male sterility and breeding of photoperiod sensitive genic male–sterile lines in rick (*Oryza sativa L.*) through anther culture," *Euphytica*, 94:93–99 (1997).

*Primary Examiner*—Paula Hutzell
*Assistant Examiner*—Melissa L. Kimball
*Attorney, Agent, or Firm*—Rothwell, Figg, Ernst & Manbeck

[57] ABSTRACT

A method is disclosed for creating and utilizing genetic male-sterile Catharanthus for hybrid periwinkle production. The method makes use of a mutated male sterility allele which suppresses pollen production in otherwise fertile plants. Individual plants expressing the male sterility factor are incapable of self pollination and can be used as female parents in hybrid seed production. Methods are disclosed for transferring this system into any inbred line of interest for use in hybrid seed production in Catharanthus.

18 Claims, No Drawings

METHOD OF PRODUCING HYBRID CATHARANTHUS USING MALE STERILITY

BACKGROUND OF THE INVENTION

The present invention relates to a Catharanthus (also called periwinkle) seed, a Catharanthus plant, Catharanthus variety, and a Catharanthus hybrid which contain a male sterility gene. This invention further relates to a method for producing a Catharanthus ($F_1$) hybrid seed and plants.

Field crops including ornamentals, are bred and produced through methods that take advantage of the plant's method of pollination. Self-pollinated crops, including all existing commercial varieties of Catharanthus, rely on the ability of a flower to transfer functional pollen from its anthers to its stigma, thus resulting in formation of seeds. If a line is true breeding for selected desirable characters, and is self-pollinated, then uniform progenies result that can be marketed as uniform cultivar varieties. Repeated selfing or inbreeding, however, results in genetic weakness, variously described as inbreeding depression.

Male sterility is a condition in plants in which male gametophytic function is prevented, but the potential for female reproduction remains. Based on inheritance patterns, there are two general types of male sterility: 1) genic or nuclear male sterility (GMS); and 2) cytoplasmic male sterility (CMS). Male-sterile mutations provide source material for studies in plant breeding, genetics, reproductive biology, and molecular biology.

An alternative to the self-pollinated Catharanthus varieties are $F_1$ hybrids. In $F_1$ hybrid varieties, pollen from an inbred "male" line is used to pollinate an inbred, but genetically different "female" line. The resulting $F_1$ hybrids are both phenotypically uniform and vigorous. In addition to this hybrid vigor, hybrids also offer opportunities for the rapid and controlled deployment of dominant genes for resistance to diseases and pests. A homozygous dominant gene in one parent of a hybrid will result in all $F_1$ hybrids expressing the dominant gene phenotype. In ornamentals, certain flower color phenotypes can only be achieved in the heterozygous state of $F_1$ hybrids.

Much progress has been made in the improvement of horticultural and agronomic crops over the past several decades. Prominent among the methods used has been that of $F_1$ hybrid seed production. Essentially all corn, tomato, cucumber, and vegetable crops in general, are grown from $F_1$ hybrid seed. Ornamentals including petunias, geraniums, impatiens, snapdragons, and many others are grown as $F_1$ hybrids. Within the seed trade industry, $F_1$ hybrids command the preeminent role because of their superior vigor, uniformity and performance.

The efficient prevention of self-fertilization is a key requirement in $F_1$ hybrid seed production. In ornamentals, such as petunia or Catharanthus, uniformity is very important since even a small level (such as 1%) of selfs can destroy the commercial value of the $F_1$ seed crop. Various methodologies are used to prevent selfing in the female. Emasculation, manual removal of anthers prior to anther dehiscence, is the primary means of preventing selfing in soybeans, tomatoes, petunias and numerous other crops. The emasculation operation in ornamentals is both logistically difficult (since a single flower cannot be overlooked and missed) and expensive because of its labor intensiveness. Some crops, such as Catharanthus, are unsuited to commercial emasculation since the flower parts prior to dehiscence are too small for commercial-level manual manipulation. Self incompatibility (SI) has also been utilized as a means of preventing accidental selfing in the female. Besides environmental instability (reversions to self-compatibility dependent on climate), the complexity of the production of inbred lines can be a major drawback in use of self-incompatibility. The absence of SI in any *Catharanthus taxa* (see Veyret, Candollea 29:297–307; Levy et al., Euphytica 32: 557–564 (1983)) precludes its utilization to prevent self-fertilization in $F_1$ hybrid seed production. Another method for prevention of accidental selfing includes application of chemical hybridizing agents (see Chia and Ruminski, J. Agric. Food Chem 39: 2072–2076 (1991)) that suppress pollen function; these agents are not used in flower seed production due to their cost, environmental instability, inconsistent and incomplete effectiveness, and their potential toxicity to greenhouse personnel. No male chemical sterilants are currently registered for greenhouse use on ornamental crops.

Dioecism, a naturally occurring phenomenon in some species wherein individual plants produce male or female parts, but not both, effectively prevents self-pollination. Unfortunately, few species of economic consequence are dioecious. Dioecy is not present in any Catharanthus species, nor has it been reported elsewhere in the Apocynaceae family.

Male sterility, both naturally occurring and artificially induced, is another means of achieving prevention of self-pollination in plants, aside from manual emasculation. In male sterility (MS) systems, absence of pollen in normally hermaphroditic flowers precludes the possibility that flowers will pollinate themselves. Without access to pollen, sexual fusion of the male and female gametes that would normally lead to seed development does not occur; the end consequence is that no "self" seed (i.e. seed arising from self-pollinations) is produced.

In higher plants, two major types of male sterility can be distinguished according to their genetic control. Nuclear male sterility (NMS), sometimes referred to as genic, genetic, or Mendelian sterility is controlled by genes carried and expressed within the nucleus of cells. Inheritance of NMS typically follows normal Mendelian segregation patterns. In contrast, cytoplasmic male sterility (CMS) is governed by cytoplasmic factors, principally the mitochondrial genome; inheritance of CMS does not follow Mendelian patterns and instead, is associated with maternal transmission of mitochondrial components from generation to generation. Neither NMS or CMS is known to occur in any Catharanthus species, nor are they known to occur naturally elsewhere in the Apocynaceae family.

Catharanthus species rely heavily on self-pollination for natural seed production. Lack of self-incompatibility, dioecy, or male sterility in any Catharanthus species indicates that self-pollination and self-set seed is an important and universal component of the reproductive biology of periwinkle species. For effective commercial production of $F_1$ hybrid Catharanthus cultivars, a more reliable system to produce $F_1$ hybrid seed is desirable. Use of a reliable male sterility gene in Catharanthus, if available, would result in efficient commercial production of hybrid Catharanthus.

SUMMARY OF THE INVENTION

The present invention relates to a Catharanthus seed, a Catharanthus plant, a Catharanthus variety, a Catharanthus hybrid and a method for producing hybrid Catharanthus seed. More specifically, the invention relates to a Catharanthus plant having the male sterile gene of the present invention.

The present invention further relates to a method of producing hybrid Catharanthus seeds using a male sterility system. The present invention further relates to a method of producing $F_1$ hybrid Catharanthus seed wherein said Catharanthus seed comprises less than 1.0% self-pollinated seed. The present invention also relates to a method of producing hybrid Catharanthus seeds and plants by crossing a male sterile plant of the instant invention with another Catharanthus plant. The present invention further relates to a method of producing seed by growing male sterile single cross Catharanthus seeds interspaced in a field with male fertile pollinator plants. The invention also relates to the transfer of the genetic male sterility gene into other genetic backgrounds.

DETAILED DESCRIPTION OF THE INVENTION

In order to provide an understanding of several of the terms used in the specification and claims, the following definitions are provided.

Hybrid—As used herein, the term "hybrid" is intended to refer to first generation $F_1$ progeny from crossing two non-identical parental lines. Parental lines may be related, as in production of a modified single cross, or unrelated.

Inbred Line—As used herein, an "inbred line" is a group or set of related plants reproduced by inbreeding which are phenotypically and genotypically similar.

Self-Pollinated Seed—As used herein, a "self-pollinated seed" means the seed arising from fusion of male and female gametes produced by the same plant. In hybrid seed production, self-pollinated seed refers to that portion (e.g., less than 1%) of the seed within a single capsule that was fathered by the female genotype rather than the intended "male" parent.

Genetic studies were conducted with the new male-sterile, female fertile Catharanthus mutant of the present invention. This mutant was completely male-sterile and was inherited as a single recessive gene designated "msGS".

To date, there is no known male sterility gene in Catharanthus other than the present invention. The mutant allele of the present invention allows seed set on the female plants. The genetic data indicate the male-sterile Catharanthus ("ms") of the present invention is genic male-sterile and is controlled monogenetically by a single recessive allele.

The male sterility system of the present invention enables the commercial production of hybrid Catharanthus. Integral to the method is reduction of self pollination to less than 1% in the designated female parent. Reduction of selfing in the female was accomplished by introduction of the male sterility (MS) gene of the present invention into the intended female line. Segregation of the MS gene in subsequent generations was monitored by presence/absence of functional pollen. Progeny derived from self-pollinated plants were scored for presence of MS segregates as well as ornamentally valuable horticultural traits. Eventually, suitable female plants were identified that are MS as well as horticulturally suitable.

Male, or "pollen" lines, do not carry the MS gene. These lines are specifically selected to produce copious amounts of highly viable pollen, as assessed by methods known to those skilled in the art. Male lines are also selected for desirable horticultural traits including, but not limited to flower color, plant height and plant habit. Pollen from the male is collected using common methods known to those in the art.

Experimental $F_1$ hybrid seed is produced by pollination of the female line (having msGS) with pollen from the male line. The $F_1$ seed is germinated and grown to maturity using standard methods common to the nursery trade. The resulting $F_1$ generation is assessed for phenotypic uniformity, vigor and horticultural suitability. By monitoring inheritance of known recessive genetic traits carried in the female, (especially flower color) and their disappearance in the $F_1$ generation due to expression of dominate alleles from the male parent, the lack of selfing in the female was confirmed. Segregation of MS in subsequent generations further clarifies the genetic nature of the MS system. After horticulturally appropriate female-male combinations are found, the corresponding male and female lines can be mass propagated and placed into commercial $F_1$ seed production. Catharanthus is readily propagated by vegetative cuttings although seed propagation of both parents is also possible using common methods routinely employed in hybrid seed production.

Methods for mutagen-induced male sterility were used (Dawson, et al., Can. J. Bot. 71:629–638 (1993) Reynaerts et al., Scientia Hort. 55: 125–139 (1993)) to produce male sterility in Catharanthus. Once the male steriles were identified, extensive genetic testing to ascertain genetic control of the MS phenomenon revealed that the generated trait of the present invention was controlled by a recessive allele.

Deployment of the male sterile allele of the present invention in Catharanthus enables commercial $F_1$ hybrid seed production which is otherwise unattainable due to the propensity in Catharanthus towards selfing and restrictions on manual emasculation caused by small flower size. By using the method of the present invention, $F_1$ hybrid Catharanthus not only possesses profound vigor advantages but also provides opportunity for commercial production of unique colors, habits and other horticulturally interesting traits achievable only in the heterozygous state.

By pollinating a homozygous female with a homozygous but genetically different male, resultant progeny will be heterozygous for any given gene locus. In breeding development of the parents, genetic backgrounds of the male and female are kept separate and intentionally selected for genetic divergence. When finally united in the $F_1$ generation, heterozygosity for a large number of gene loci imparts broad-based hybrid vigor with controlled deployment of dominant alleles expressed in the hybrid.

EXAMPLES

The following examples are provided to further illustrate the present invention and are not intended to limit the invention beyond the limitations set forth in the appended claims and amendments.

Example 1

Overview of the Method of Developing $F_1$ Hybrids

Production of $F_1$ hybrid seed in Catharanthus utilizes MS expressed in the female or "seed" parent. By possessing MS of the present invention, the female is unable to self pollinate; as such, self-set seed is not produced. In breeding development of the female, horticulturally desirable traits are accumulated in the female line using methods known to those in the art. The female line is repetitively inbred or sib-crossed. At a later stage in the breeding process, MS females are identified that lack functional pollen and that are potentially suitable for use in commercial seed production.

The male or pollen parent is similarly bred for desirable horticultural qualities using methods known to those in the art. Unlike the female, pollen quality and quantity are an important selection component in the developmental breeding process of the male.

When appropriate male and female lines have been constructed, pollinations are performed wherein pollen is removed from the male plant using methods known to those skilled in the trade, and transferred to female receptive stigmas. Subsequent to these pollinations, normal seed development processes occur in the female plant ultimately resulting in seed formation. Numerous experimental male and female combinations are tried, resulting in many experimental $F_1$ hybrid progenies. Each progeny is then evaluated for presence of characters deemed horticulturally desirable. Genetic markers (such as color difference) can be used to ascertain complete absence of self-set seed from the female. Eventual evaluation of various male/female combinations can lead to appropriate combinations which can then be used in commercial $F_1$ hybrid seed production.

Example 2

Development of the MS Gene

Male Sterility was not known to occur in any Catharanthus germplasm. All available Catharanthus germplasm was screened for existence of possible spontaneous male sterility such as that found in tomato as discussed by Gorman and McCormick, *Critical Reviews in Plant Sciences* 16:31–53 (1997). Levy et al., Euphytica 32: 557–564 (1983) confirm the absence of male steriles in *Catharanthus roseus*. Beginning in 1992, attempts were made to induce mutations resulting in male sterility. Chemical mutagens including, but not limited to EMS (methane sulfonic acid ethyl ester), and antibiotics (Mitomycin C, Streptomycin) were used. Jan and Rutger, *Crop Science* 28: 792–795, reported that streptomycin could be used for induction of CMS in sunflower. Following the treatment methods of Jan and Rutger (loc cit.), seeds of *Catharanthus roseus* were treated with streptomycin and subsequently grown to flowering maturity. From approximately 400 induced seedlings, two plants were identified that lacked mature normal-looking pollen. These plants (13861-1, 13861-2) were allowed to grow for a two year period of time and rigorously checked for presence of any self-set seed under changing climate and plant maturity states. Though initially male sterile, plant 13861-2 eventually did produce a small number of self-set seeds indicating that it was only conditionally or partially male sterile. Partial male sterility has been commonly reported elsewhere (U.S. Pat. No. 3,861,079; U.S. Pat. No. 4,654,465) and is frequently encountered in induced mutation attempts aimed at male sterility (Jan and Rutger, loc. Cit.; Singh, I. S., Ann. Amelior. Plantes 258: 303–319 (1975)). Plant 13861-1 continuously failed to self-set seed and was investigated further to demonstrate female fertility.

Example 3

A Genetic Basis for MS in Catharanthus

Plant 13861-1 was used as a female in crosses with various Catharanthus cv. pollen donors. (Table 1). Pollinated flowers in these crosses produced fruits and seeds, demonstrating female fertility in plant 13861-1. These seeds were germinated and grown using standard methods known to those in the nursery industry. Resultant progenies were scored for presence/absence of viable pollen as well as inheritance of horticultural characters (e.g., flower color, habit). Presence of dominant genetic markers in $F_1$ progeny clearly demonstrated that progeny were true hybrids and not apomictic.

As shown in Table 1, all $F_1$ hybrid progeny are pollen fertile, an observation consistent with diallelic recessive allele control, such as reported in corn (Patterson, U.S. Pat. No. 3,861,079). Selfing of $F_1$ progenies (See Table 1) further confirms that MS in the initial male sterile plant (13861-1) was controlled be a recessive allele. Finally, as shown in Table 2, test crosses definitively demonstrate that the MS phenotype is controlled by a recessive allele.

TABLE 1

Segregation of MS in out crosses where 1386-1 is used as the female parent

| Cross Number | Male Parent | $F_1$ Progeny Segregation Fertile/Sterile | $F_2$ Cross Number | Observed Fertile/Sterile Ratio |
|---|---|---|---|---|
| 14682 | 13022-5 | 1:0 | 15781 | 3:1[a] |
| 14780 | 13516-3 | 1:0 | 15682 | 3.1[a] |
| 14781 | 13534-34 | 1:0 | 15674 | 3:1[a] |
| 14783 | 13658-23 | 1:0 | 15675 | 3:1[a] |
| 14790 | 13516-17 | 1:0 | 16083 | 3:1[a] |
| 14847 | 14590-10 | 1:0 | 16070 | 3:1[a] |
| 14848 | 14589-12 | 1:0 | 16064 | 3:1[a] |
| 14849 | 13658-13 | 1:0 | 16065 | 3:1[a] |
| 14856 | 13518-34 | 1:0 | 16039 | 3:1[a] |
| 14865 | 13500-* | 1:0 | 15703 | 3:1[a] |
| 14936 | 13658-58 | 1:0 | 17157 | 3:1[a] |
| 14937 | 13658-47 | 1:0 | 16049 | 3:1[a] |
| 15014 | 13658-59 | 1:0 | 17152 | 3:1[a] |
| 15015 | 13658-60 | 1:0 | 17153 | 3:1[a] |
| 15108 | 13658-28 | 1:0 | 16209 | 3:1[a] |
| 15109 | 13658-39 | 1:0 | 16211 | 3:1[a] |
| 15110 | 13658-34 | 1:0 | 16212 | 3:1[a] |
| 15111 | 13658-37 | 1:0 | 16210 | 3:1[a] |
| 15166 | 13435-1 | 1:0 | 17202 | 3:1[a] |
| 15167 | 13516-22 | 1:0 | 16659 | 3:1[a] |
| 15217 | 14799-* | 1:0 | 16213 | 3:1[a] |
| 15359 | 13516-17 | 1:0 | 17235 | 3:1[a] |
| 15672 | 14804-3 | 1:0 | 17066 | 3:1[a] |
| 15673 | 14804-6 | 1:0 | 17238 | 3:1[a] |

[a]Significant ratio based on Chi Square $P < .05$.

Example 4

Deployment of Catharanthus msGS

Subsequent to induction and capture of msGS gene, numerous crosses between existing Catharanthus cultivars and the MS background were made as shown in Table 2. Advanced generations ($F_2$, $F_3$, etc) from these crosses confirm, in every instance, that MS in Catharanthus is inherited in a normal fashion consistent with recessive nuclear control. Moreover, that $F_1$ seed can be produced at all indicated that female function (ovule and seed production ability) is unaffected in MS lines. $F_1$ seed yield is at least equivalent to intentionally selfed Catharanthus flowers, suggesting that the MS gene specifically affects male function rather than overall fertility aspects.

TABLE 2

Test crosses involving the MS gene

| Cross Number | $F_1$ Hybrid Male Parent[a] | Female Parent[b] | Expected MS Segregation | Observed MS Segregation |
|---|---|---|---|---|
| 15677 | 14781-7 | 13861-1 | 1:1 | 1:1[c] |
| 15678 | 14781-30 | 13861-1 | 1:1 | 1:1[c] |
| 15679 | 14780-30 | 13861-1 | 1:1 | 1:1[c] |
| 15680 | 14780-47 | 13861-1 | 1:1 | 1:1[c] |
| 15681 | 14783-3 | 13861-1 | 1:1 | 1:1[c] |
| 15900 | 14369-1 | 13861-1 | 1:1 | 1:1[c] |

TABLE 2-continued

Test crosses involving the MS gene

| Cross Number | F₁ Hybrid Male Parent[a] | Female Parent[b] | Expected MS Segregation | Observed MS Segregation |
|---|---|---|---|---|
| 15901 | 14804-2 | 13861-1 | 1:1 | 1:1[c] |
| 15902 | 14804-5 | 13861-1 | 1:1 | 1:1[c] |
| 15903 | 14368-1 | 13861-1 | 1:1 | 1:1[c] |
| 15904 | 14368-5 | 13861-1 | 1:1 | 1:1[c] |
| 15937 | 14925-12 | 13861-1 | 1:1 | 1:1[c] |
| 15938 | 14925-20 | 13861-1 | 1:1 | 1:1[c] |
| 15939 | 14925-26 | 13861-1 | 1:1 | 1:1[c] |
| 15940 | 14927-8 | 13861-1 | 1:1 | 1:1[c] |
| 15945 | 13522-6 | 13861-1 | 1:1 | 1:1[c] |
| 15949 | 13069-74 | 13861-1 | 1:1 | 1:1[c] |

[a]See Table 1 for origin of these individuals.
[b]Phenotypically male sterile; this is the same genotype that was used as the female in Table 1.
[c]Significant ratio based on Chi Square P < .05

Example 5

Mode of Action of the MS Gene

Microscopic examination of anthers in MS Catharanthus plants reveals absence of intact functional pollen. Early microsporocytes and microspores appear normal indicating meiotic aberrations are unlikely explanations for the observed MS. Male sterile mutants (Dawson et al., *Can. J. Bot.* 71:629–638 (1993); Loukides et al. *Am J. Bot* 82: 1017–1023(1995) have been associated with abnormal tapetal cell development. Tsuchiya et al. (Plant cell Physiol. 36: 487–497(1995) have shown that aberrant callose deposition beginning at the tetrad stage can explain their observed MS. Observed disruptive pollen development in Catharanthus, resulting in partial (13861-2) or total MS (13861-1) is consistent with models of disrupted callose activity resulting in MS.

Example 6

Pleiotropic Effects of MS in Catharanthus

Bar and Frankel (Euphytica 69: 149–154(1993) have studied the influence of seven recessive MS alleles on total marketable yield of F₁ hybrid tomatoes. They concluded that some MS alleles affect the general combining ability of female lines. The Catharanthus msGS gene of this invention has been crossed into available cultivar germplasm as indicated in Table 3. No significant non-combining ability has been observed beyond expected variation in fertility commonly associated in inter-cultivar crosses as would be encountered by breeders familiar with the art. No linkages between the msGS gene of this invention and other significant horticultural traits (e.g. flower color, plant size, habit, etc.) have been observed.

Example 7

Transfer of msGS Allele in Numerous Genetic Backgrounds

As shown in Table 3, the msGS allele of the present invention was crossed into multiple Catharanthus cultivars. In each of these backgrounds the msGS allele segregated as expected for a single recessive allele.

TABLE 3

Catharanthus cultivars, which when crossed to msGS, segregate male sterility as expected Little Pinkie
Little Bright Bye
Little Blanche
Little Delicata
Pretty in Pink
Pretty in White
Pretty in Rose
Tropicana Rose
Tropicana Bright Bye
Tropicana Pink
Tropicana Blush
Peppermint Cooler
Grape Cooler
Morning Mist
Pacifica Red
Pacifica White
Pacifica Pink
Pacifica Blush
Apricot Delight Example 8

Isolation and Characterization of the msGS Gene

The male sterility gene of the present invention is a DNA sequence encoding for the observed male sterility phenotype. By using the method of DeCarolis and DeLuca (Plant Cell Tissue Culture 38:281–287 (1994), herein incorporated by reference, the msGS gene is isolated and characterized. Kai, et al., (Soil Sci. Plant Nutr. 43:227–235 (1997), herein incorporated by reference, describe the methodology employed for isolation and characterization of a cDNA from *Catharanthus roseus*. Using the methods of Kai, et al., the msGS gene is isolated from Catharanthus tissues, purified, and structurally characterized, based on analysis of its DNA sequence.

Example 9

Transformation Using the Male Sterility Gene msGS from Catharanthus

Following isolation and characterization of the male sterility gene msGS, existing transformation protocols well known in the art can be used to insert the gene into other plant species. Hallard, et al., (Plant Cell Reports 17:50–54 (1997), herein incorporated by reference, transformed *Nicotiana tabacum* with genes extracted from *Catharanthus roseus;* and described activity of the periwinkle genes in the foreign genetic background, following combination of the genes with appropriate promoters and insertion into tobacco cells and tissues using standard transformation procedures well known in the art. By using the isolated gene sequences for the male sterility gene msGS, as described in Example 8, the male sterility gene is combined with a promoter and transformed into other plant species, such as tobacco. After the msGS gene is inserted in the host species, the male sterility gene of the present invention is expressed in the host species.

Deposit Information

Hybrid Catharanthus 19238 using male sterility seeds of the instant invention have been placed on deposit with the American Type Culture Collection (ATCC), Manassas, Va., under Deposit Accession Number 203176 on Sep. 1, 1998.

Although the foregoing invention has been described in some detail by way of illustration and example for purposes of clarity and understanding, it will be obvious that certain changes and modifications may be practiced within the scope of the invention.

What is claimed is:

1. A Catharanthus seed containing an allelic DNA genetic factor for male sterility designated msGS and deposited under ATCC Accession No. 203176.

2. The Catharanthus seed of claim 1, wherein said seed contains a recessive allele for male-sterility.

3. A Catharanthus plant produced by growing the seed of claim 1.

4. Pollen of the plant of claim 3.

5. An ovule of the plant of claim 3.

6. A method for producing $F_1$ hybrid Catharanthus seed comprising crossing a first parent Catharanthus plant with a second parent Catharanthus plant and harvesting the resultant $F_1$ hybrid Catharanthus seed, wherein said first or second parent Catharanthus plant is the Catharanthus plant of claim 3.

7. A hybrid seed produced by the method of claim 6.

8. A hybrid plant or its parts produced by growing said hybrid seed of claim 7.

9. Seed containing said genetic factor for male sterility designated msGS produced from said hybrid plant of claim 8.

10. The method of claim 6, wherein said hybrid Catharanthus seed produced comprises less than 1.0% self-pollinated seed.

11. The method of claim 10, wherein said Catharanthus seed produced comprises between about 0.80% and about 0.99% self-pollinated seed.

12. The method of claim 10, wherein said Catharanthus seed produced comprises between about 0.60% and about 0.79% self-pollinated seed.

13. The method of claim 10, wherein said Catharanthus seed produced comprises between about 0.40% and about 0.59% self-pollinated seed.

14. The method of claim 10, wherein said Catharanthus seed produced comprises between about 0.20% and about 0.39% self-pollinated seed.

15. The method of claim 10, wherein said Catharanthus seed produced comprises between about 0.01% and about 0.19% self-pollinated seed.

16. The method of claim 6, wherein said Catharanthus plant of claim 3 is the female plant.

17. A plant cell of a first generation ($F_1$) hybrid Catharanthus plant produced by growing said hybrid Catharanthus seed of claim 7.

18. Viable Catharanthus seeds deposited under ATCC Accession No. 203176 on Sep. 1, 1998 and plants grown from said deposited seeds and the progeny thereof, wherein the progeny contain the male sterile allele designated msGS.

* * * * *